US008269971B1

(12) United States Patent
Marsh et al.

(10) Patent No.: US 8,269,971 B1
(45) Date of Patent: Sep. 18, 2012

(54) SYSTEM AND METHOD FOR SIMULTANEOUS DETECTION OF A GAS USING A MODE-LOCKED BASED TRANSMITTER

(75) Inventors: Waverly Dickson Marsh, Vienna, VA (US); Steven Vincent Stearns, Vienna, VA (US)

(73) Assignee: Exelis, Inc., McLean, VA (US)

( * ) Notice: Subject to any disclaimer, the term of this patent is extended or adjusted under 35 U.S.C. 154(b) by 397 days.

(21) Appl. No.: 12/617,210

(22) Filed: Nov. 12, 2009

(51) Int. Cl.
*G01N 21/00* (2006.01)
(52) U.S. Cl. .......................... 356/437; 356/432; 356/436
(58) Field of Classification Search ........... 356/432–444
See application file for complete search history.

(56) References Cited

U.S. PATENT DOCUMENTS

| | | | | |
|---|---|---|---|---|
| 4,746,218 | A * | 5/1988 | Lord, III | 356/437 |
| 5,015,099 | A * | 5/1991 | Nagai et al. | 356/437 |
| 6,995,846 | B2 | 2/2006 | Kalayeh et al. | |
| 7,508,520 | B1 * | 3/2009 | Lines et al. | 356/437 |
| 2005/0134859 | A1 * | 6/2005 | Kalayeh et al. | 356/437 |
| 2006/0262311 | A1 * | 11/2006 | Muta et al. | 356/437 |

OTHER PUBLICATIONS

Babichenko, Segey; Dudelzak, Alex; and Poryvkina, Larisa, "Laser Remote Sensing of Coastal and Terrestrial Pollution by FLS-Lidar," EARSel eProceedings 3, pp. 1-7, Jan. 2004.

Phillips, P.J.; Das, S.; Ebrahimzadeh, M., High-Repetition-Rate, All-Solid State, Ti:Sapphire-Pumped Optical Parametric Oscillator for the Mid-Infrared, Applied Physics Letters, vol. 77, pp. 469-471, Jul. 24, 2000.

Delfyett, Peter J., Shi, H.; Gee, S.; Barty, Christopher P.J.; Alphonse, G.; and Connolly, J., 'Intracavity Spectral Shaping in External Cavity Mode-Locked Semiconductor Diode Lasers', IEEE Journal of Selected Topics in Quantum Electronic, vol. 4, No. 2, Mar./Apr. 1998.

* cited by examiner

*Primary Examiner* — Michael P Stafira
(74) *Attorney, Agent, or Firm* — RatnerPrestia

(57) ABSTRACT

A remote sensing system includes a transmitter for generating multiple beams of light; a combiner for combining the multiple beams of light and directing the combined multiple beams toward a target of multiple gases; and a receiver for receiving the combined multiple beams of light from the target. The first and second transmitted beams of light include, respectively, first and second sets of multiple distinct wavelengths that are simultaneously transmitted toward the target. The receiver receives the multiple distinct wavelengths, and simultaneously detects an intensity of each received wavelength. The first set of multiple distinct wavelengths is selected based on absorption characteristics of a first species of gas, and the second set of multiple distinct wavelengths is selected based on absorption characteristics of a second species of gas. The transmitter includes first and second mode-locked based lasers for generating, respectively, the first and second sets of distinct multiple wavelengths. The receiver includes first and second pixel arrays for detecting, respectively, the first and second sets of distinct multiple wavelengths.

19 Claims, 6 Drawing Sheets

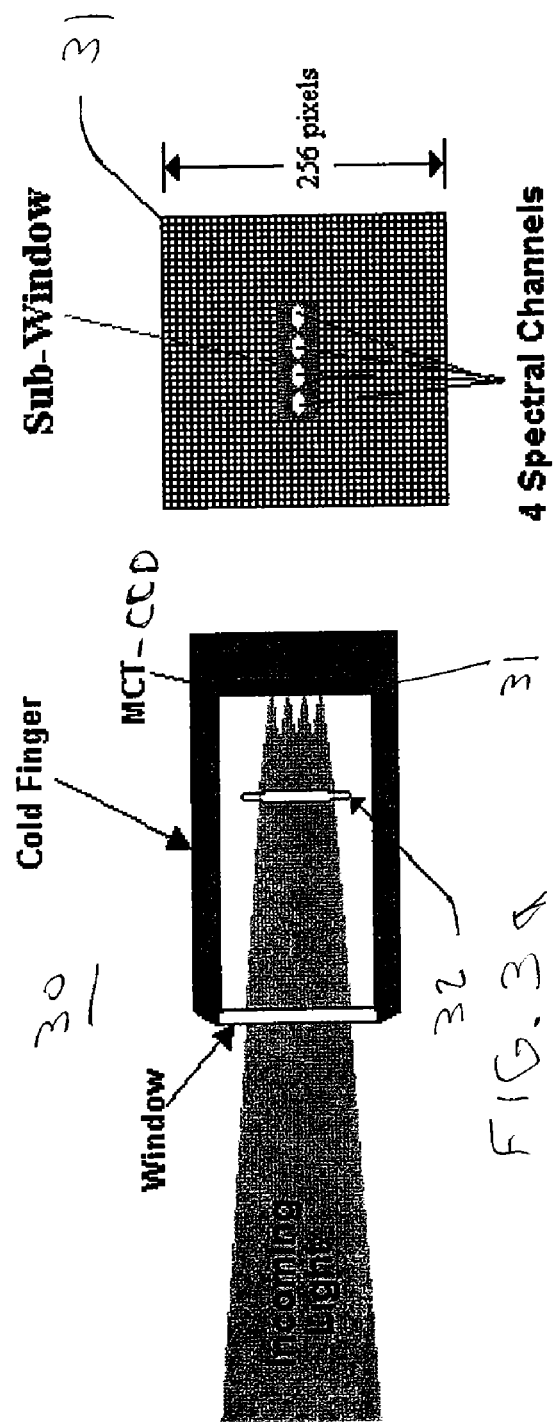

SYSTEM AND METHOD FOR SIMULTANEOUS DETECTION OF A GAS USING A MODE-LOCKED BASED TRANSMITTER

FIELD OF INVENTION

The present invention relates, in general, to a system and method for detecting multiple gasses in the atmosphere using laser transmitters. More specifically, the present invention relates to remotely detecting the presence of multiple gasses by transmitting multiple spectral channels in a single optical beam, which are generated by a mode locked laser based transmitter. For example, the present invention may simultaneously detect methane and carbon dioxide in the atmosphere.

BACKGROUND OF THE INVENTION

Referring to FIG. 6, there is shown a conventional remote sensor located in an aircraft which may be used for identifying a substance in the atmosphere. As shown, remote sensor 60 includes optical transmitter 62 for transmitting an optical beam through a substance of interest towards the earth (hard target). The optical beam, which is reflected from the earth, passes again through the substance of interest and received by optical receiver 63. A data acquisition system, generally designated as 61, analyzes the returned beam, which may be greatly attenuated by the substance of interest. The data acquisition system makes a determination about the quantity and/or the identity of the substance of interest.

The conventional sensor system 60 may be a differential absorption light detecting and ranging (LIDAR) system, or simply a DIAL system. The DIAL system is an active remote sensing based instrument including two or more pulsed laser transmitters which transmit different colors at separate time intervals to probe the atmosphere below the aircraft. Ground reflected light from these lasers is measured by a receiver including photodiodes.

One wavelength of one of the laser transmitters is tuned to an absorption wavelength of methane (for example) in the mid wave infrared part of the electromagnetic spectrum (known as the online wavelength). One (or more) wavelengths of other laser transmitter(s) are tuned to a wavelength near but not on an absorption wavelength of methane (known as the offline wavelength(s)). An optical receiver measures both the outgoing laser intensities and the backscattered ground return intensities. The online and offline wavelengths are measured by time differences in transmitted and returned spectral content. Concentration measurements of methane are made using algorithm calculations based on these optical measurements.

Another conventional sensor system 60 may be an active remote sensing system which does not use pulsed optical signals, but uses two or more continuous wave (CW) laser sources. The CW signals are combined and transmitted below the airborne platform. Different color CW beams may be combined by an optical combiner, such as a fiber optic or an optical mask, and transmitted downwardly as a single beam. The light in this transmitted beam may include online and offline wavelengths in the near infrared wavelength band, near 1.2-1.5 microns (for example).

These exemplary wavelengths are characteristic of specific carbon dioxide ($CO_2$) and oxygen ($O_2$) absorption features. Ground returns from these transmitted wavelengths may be collected in a fiber optic based receiver, where different color content may be measured by a demodulation technique similar to an FM radio receiver, but designed for near infrared wavelengths. Spectral content of the transmitted and returned beams may be used to determine $CO_2$ concentrations based upon these optical measurements. The $O_2$ channel wavelengths may be used for air temperature and pressure compensation corrections, which are needed during high altitude operation.

Even in a differential technique, such as DIAL, which is designed to reduce noise factors, factors such as atmospheric interference, irregular surface reflectance, object interference (bushes, trees, power line, etc.), source laser misalignment, source laser energy distribution and relative motion between the remote sensing platform and the target may lead to poor data quality. This poor data quality, in turn, may lead to missed detection or false positive detection.

For most DIAL techniques, conventional systems use two lasers (or one laser that produces two wavelengths) in which one laser is designated the online laser and the other laser is designated the offline laser. The online laser signal is designed to be absorbed by the chemical species of interest, while the offline laser signal is designed not to be absorbed by the chemical species of interest. By measuring the transmitted and returned energies for both lasers and applying a differential data processing technique, one may measure the path-integrated concentration, or concentration path-length product (also referred to as the concentration path length (CPL)) of the chemical species in the column of air to a particular target location. This differential measurement helps reduce noise factors but the measurement may further be refined by allowing a longer sample exposure or by integrating samples of the same column of air. However, this tends to defeat one of the advantages of a remote sensing system which is rapid area coverage.

In general, a DIAL system, which uses pulsed optical signals and attempts to measure the concentration of $CH_4$ in a column of air, may have a limited background measurement accuracy (for example, approximately 50 ppm*m (parts per million*meter), or as another example, approximately +/−15% of the background level) The DIAL system is typically designed to locate plumes only and not calculate accurate background $CH_4$ levels. An upper range for plume quantification, for example, may be about 4000 ppm*m with reduced accuracy. The coverage rate, while flying in an aircraft, may be moderate and may typically be limited to 1.8 miles$^2$/hr, as an example. The DIAL system also may have limited detection capabilities over water.

In the other sensor system, which is described above as a CW optical system attempting to measure and quantify $CO_2$ concentrations in the atmosphere, there are also several deficiencies. There is limited plume location and quantification capability. Instrument modality requires fairly long temporal integration, due to speckle noise surrounding extremely narrow spectral content. This leads to poor ground spot resolution (GSR) for the gas measurements. Ground spot resolution is typically on the order of square miles, which limits surveys over small targets, or regions of interest.

In order to identify and quantify two types of measurements for two gasses (for example, methane and carbon dioxide), conventional active remote sensor systems would require two types of DIAL sensors and two types of CW optical systems. That is, two types of DIAL sensors would be required to provide plume quantification and background measurements for methane; and two types of CW optical sensors would be required to provide plume quantification and background measurements for carbon dioxide. This potential need for 4 sensors on one platform is considered a major drawback, if DIAL modalities are to be used for measuring greenhouse gas sources of both $CO_2$ and $CH_4$ (for example).

As will be explained, the present invention provides a system and method for improving the quality of detection and quantification of one or multiple species of gas in a column of air, when examined from an airborne platform, such as an aircraft or satellite. The platform may, of course, also be a van or a truck. In addition, the present invention provides a new type of DIAL modality using light source(s) which have sufficient spectral content to probe, or investigate the atmospheric species of gas.

As will also be explained, the present invention uses mode-locked based laser transmitters to provide stable and simultaneous broad spectral content. For example, four spectral channels may be generated simultaneously by the present invention within one single optical beam. These spectral channels are sub-bands of colors, which are resolved by a grating based receiver and measured simultaneously.

SUMMARY OF THE INVENTION

To meet this and other needs, and in view of its purposes the present invention provides a remote sensing system. The system includes a transmitter for transmitting a single beam of light toward a target, and a receiver for receiving the single beam of light from the target. The transmitted single beam of light includes multiple distinct wavelengths that are simultaneously transmitted toward the target. The receiver is configured to simultaneously receive the multiple distinct wavelengths, and detect an intensity of each received wavelength. The target includes at least one species of gas, and the multiple distinct wavelengths are selected based on absorption characteristics of the one species of gas.

At least one of the multiple distinct wavelengths is selected at a center of a wavelength distribution curve depicting the absorption characteristics of the species of gas, the center defined as an online wavelength. At least another of the multiple distinct wavelengths is selected at a wavelength location that is away from the wavelengths absorbed by the species of gas, the wavelength location defined as an offline wavelength. Yet another of the multiple distinct wavelengths may be selected at a location that is between the at least one online wavelength and the at least one offline wavelength.

The transmitter includes a mode-locked based laser for generating the distinct multiple wavelengths in the single beam of light. The receiver includes a pixel array for detecting the distinct multiple wavelengths in the single beam of light. The receiver includes a diffraction grating for separating the distinct multiple wavelengths in the single beam of light. At least one lens and/or mirror is interposed between the diffraction grating and the pixel array for focusing the distinct multiple wavelengths onto the pixel array.

A processor receives image intensity data from the pixel array and determines an identity of the target based on the detected distinct multiple wavelengths. A photodiode is connected in parallel with the receiver, for detecting intensity levels of the received single beam of light. An integrator integrates the detected intensity levels, and a saturation prevention module resets the receiver upon reaching an intensity level by the integrator. The saturation prevention module is configured to prevent saturation of the intensity levels of the multiple distinct wavelengths detected by the receiver.

The remote sensing system may include a gas cell for receiving and testing a sample of the multiple distinct wavelengths in the single beam of light, and means for adjusting the multiple distinct wavelengths, based on test results of the gas cell.

The target may include either or both of carbon dioxide or methane.

Another embodiment of the parent invention is a remote sensing system including a transmitter for generating multiple beams of light; a combiner for combining the multiple beams of light and directing the combined multiple beams toward a target; and a receiver for receiving the combined multiple beams of light from the target. A first transmitted beam of light includes a first set of multiple distinct wavelengths that are simultaneously transmitted toward the target. A second transmitted beam of light includes a second set of multiple distinct wavelengths that are simultaneously transmitted toward the target. The receiver is configured to simultaneously receive the multiple distinct wavelengths, and detect an intensity of each received wavelength.

The target may include at least two species of gas. The first set of multiple distinct wavelengths are selected based on absorption characteristics of a first species of gas, and the second set of multiple distinct wavelengths are selected based on absorption characteristics of a second species of gas.

The transmitter includes a first mode-locked based laser for generating the first set of distinct multiple wavelengths in the first transmitted beam of light. The transmitter also includes a second mode-locked based laser for generating the second set of distinct multiple wavelengths in the second transmitted beam of light. The receiver includes a first pixel array for detecting the first set of distinct multiple wavelengths. The receiver also includes a second pixel array for detecting the second set of distinct multiple wavelengths.

The receiver includes a first diffraction grating for separating the first set of distinct multiple wavelengths, and a second diffraction grating for separating the second set of distinct multiple wavelengths. The combiner includes first and second divergent setting telescopes for (a) directing the first beam and second beam, respectively, toward a beam splitting cube, and (b) focusing the first and second beams to deliver the combined beam as a predetermined sized spot on the target.

Yet another embodiment of the present invention is a method for remotely detecting a plume of gas including the steps of:

(a) transmitting a single beam of light toward the plume, and (b) receiving the single beam of light from the plume, wherein the step of transmitting includes (i) simultaneously transmitting multiple distinct wavelengths toward the plume, and the step of receiving includes (ii) simultaneously receiving the multiple distinct wavelengths, and (iii) simultaneously detecting an intensity of each received wavelength.

The step of transmitting includes selecting and generating the multiple distinct wavelengths based on absorption characteristics of the plume of gas. At least one of the multiple distinct wavelengths is selected at a center of a wavelength distribution curve depicting the absorption characteristics of the plume of gas, the center defined as an online wavelength, and at least another of the multiple distinct wavelengths is selected at a wavelength location that is away from the wavelengths absorbed by the plume of gas, the wavelength location defined as an offline wavelength. Yet another of the multiple distinct wavelengths may be selected at a location that is between the at least one online wavelength and the at least one offline wavelength.

The step of transmitting includes using a mode-locked based laser for generating the distinct multiple wavelengths. The step of receiving includes separating the distinct multiple wavelength by using a diffraction grating, and imaging the separated distinct multiple wavelengths by using a pixel array.

It is understood that the foregoing general description and the following detailed description are exemplary, but are not restrictive, of the invention

BRIEF DESCRIPTION OF THE FIGURES

The invention may be understood from the following detail description when read in connection with the accompanying figures:

FIG. 3 an exemplary pixel array module for detecting the multiple spectral wavelengths received by the remote sensing system shown in FIG. 1, in accordance with an embodiment of the present invention.

DETAILED DESCRIPTION OF THE INVENTION

The present invention includes a new type of DIAL modality, or methodology. In one embodiment, the present invention uses one or more light sources which have enough spectral content to probe (or investigate) the atmospheric species of interest. The present invention uses mode-locked based laser transmitters (or light sources) to provide stable and simultaneous broad spectral content. In one example, described below, four spectral channels are generated simultaneously within the same optical beam. These spectral channels include sub-bands of colors, which can be resolved by a grating based receiver and measured simultaneously. Furthermore, the spectral content is contained in one beam for each gas and derived from one beam, rather than a combination of separate beams. The transmitted beam may be described as a quasi-CW signal, because the beam has a fast repetition rate, which may be between approximately 10 MHz-500 MHz. For multiple gasses, multiple beams may be combined, where each beam includes multiple spectral content selected for each gas of interest.

Figure 5:
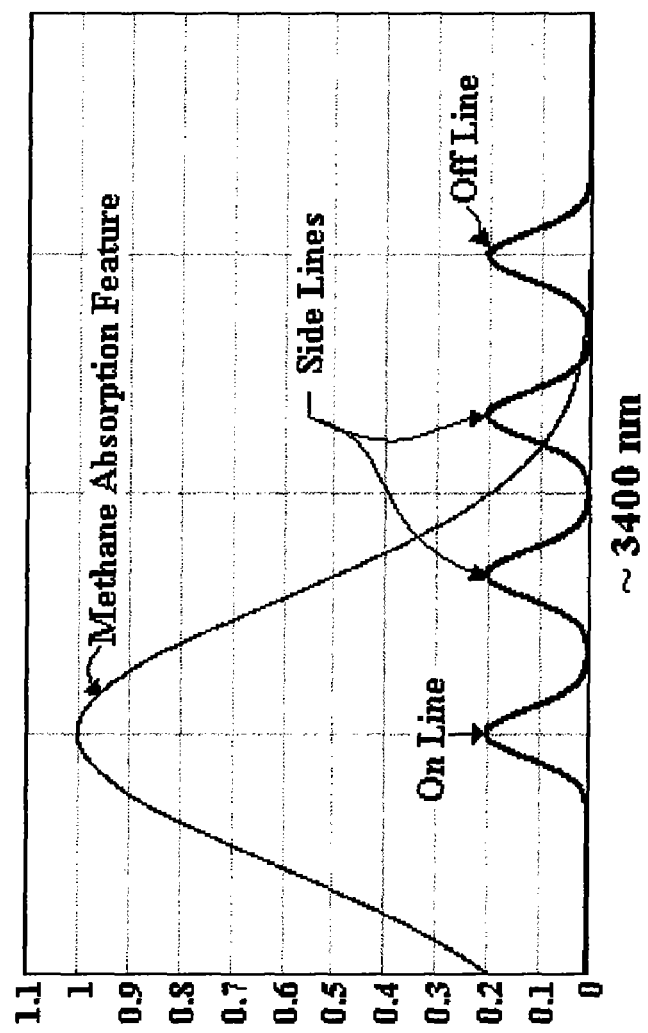
FIG. 5 depicts an exemplary selection of four spectral output lines in relations to an absorption characteristics curve of methane, in accordance with an embodiment of the present invention.
Figure 6:
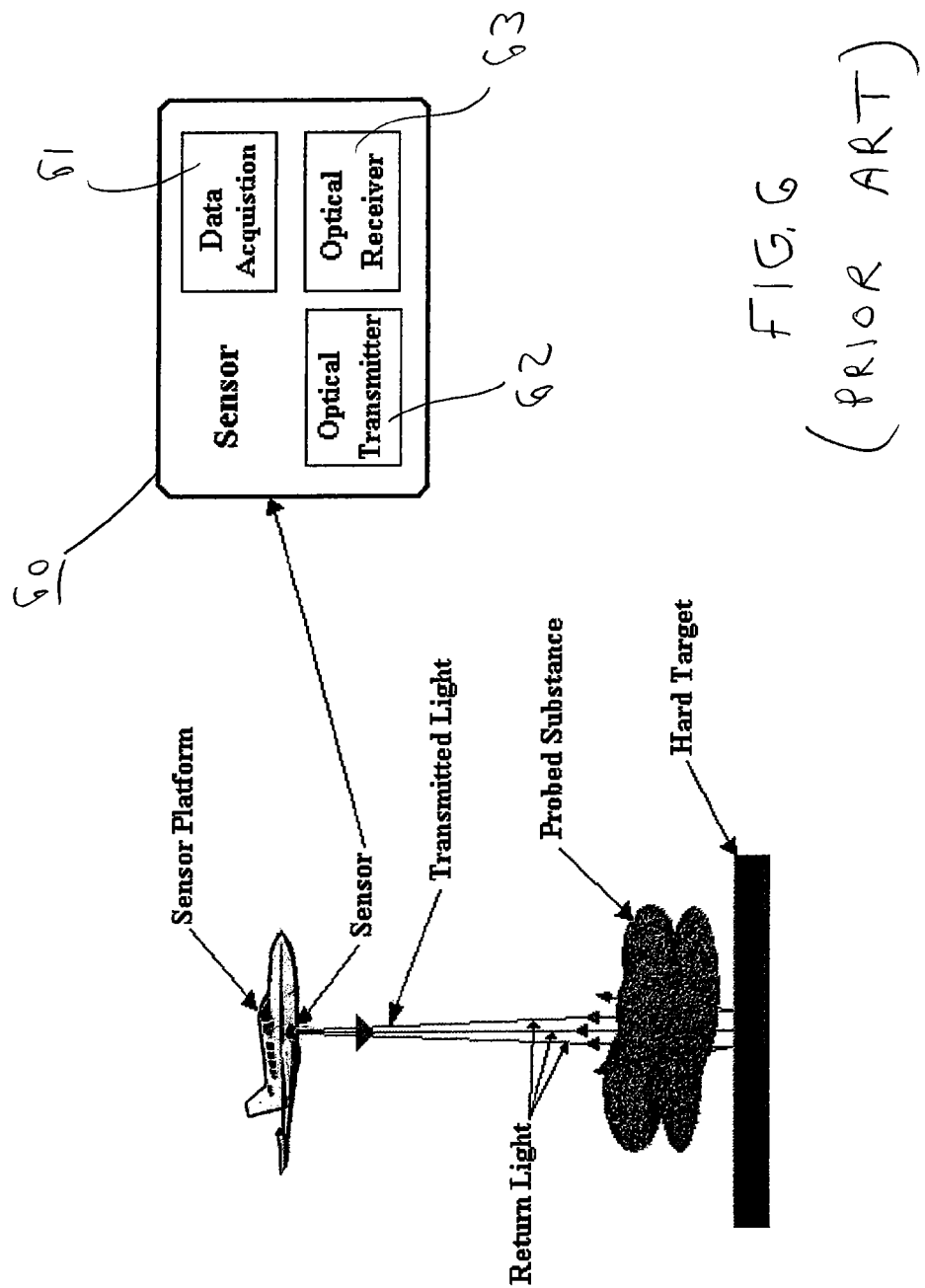
FIG. 6 is a block diagram of a conventional remote sensing system for detecting a species of gas in the atmosphere.

In this exemplary embodiment, the four spectral channels are chosen so that there is one channel on the center of an absorption feature of $CH_4$ (for example), there is one channel near but completely off the same absorption feature of $CH_4$ and there are two channels which are located on the side-line of the same absorption feature of $CH_4$. This example of four spectral channels is shown in FIG. 5.

An advantage in including two side-line channels is in increasing the sensor's dynamic range over that of a conventional DIAL system, which only has one online and one offline channels. The side-line spectral channels are not as strongly absorbed as the online channel. Consequently, when concentrated plumes of gas are encountered, the signals contained in the side-line channels provide measurement information, which improves accuracy and dynamic range.

Similarly, when detecting $CO_2$ (for example), four spectral channels are chosen so that there is one channel on the center of an absorption feature of $CO_2$, there is one channel near but completely off the same absorption feature of $CO_2$ and there are two channels which are located on the side-line of the same absorption feature of $CO_2$.

If it is desired to simultaneously detect both $CH_4$ and $CO_2$, then in a similar embodiment four spectral channels are chosen as indicated above for $CH_4$ and four other spectral channels are chosen as indicated above for $CO_2$.

The quasi-CW nature of the present invention advantageously allows variable integration time (VIT) which effectively increases the measurement rate for plume detection and quantification to about 10 kHz, as compared to 1 kHz for a conventional DIAL system. The coverage rates, as well as the swath width, scanned by the invention are also increased. The quasi-CW nature also allows finding specular reflections over water more reliably than does a conventional DIAL system.

In addition, the broadband nature of the transmitted light of the present invention advantageously reduces speckle noise (−40 to −50 dB), which deleteriously effects a conventional CW system. Speckle noise causes a CW system to require long integration time. In turn, a long integration time leads to poor ground spot resolution on the order of square miles. The speckle reducing property of the broadband nature of the transmitted light allows good ground spot resolution, which is on the order of square meters.

Further still, mode-locking a laser transmitter advantageously forms a stable spectral-power profile many times more stable than the pulsed laser transmitters used by conventional DIAL sensors. Typically, power stability of a mode-locked laser is better than 1% over a 12 hour time window. Variations in pulsed lasers, on the other hand, may be greater than 5% from one instant of time to the next.

Moreover, the present invention provides the spectral content (or spectral channels) from one single laser beam. As a result, there is little likelihood that the spectral content would probe different gas volumes in the atmosphere. The spectral content transmitted hits exactly the same ground spot, and the returned light is reflected from exactly the same ground spot. Consequently, the present invention is expected to provide a concentration accuracy that may be better than 10 ppm*m, as compared to 50 ppm*m for a conventional DIAL system. In addition, the background gas concentration may be determined to a measurement accuracy better than 0.5%, depending on the amount of integration time.

Another advantage is that the present invention only needs one modality to perform plume detection and quantification, or measure accurate background concentration for both $CO_2$ and $CH_4$, since the sensor system may use a variable time of integration for each gas.

Figure 1:
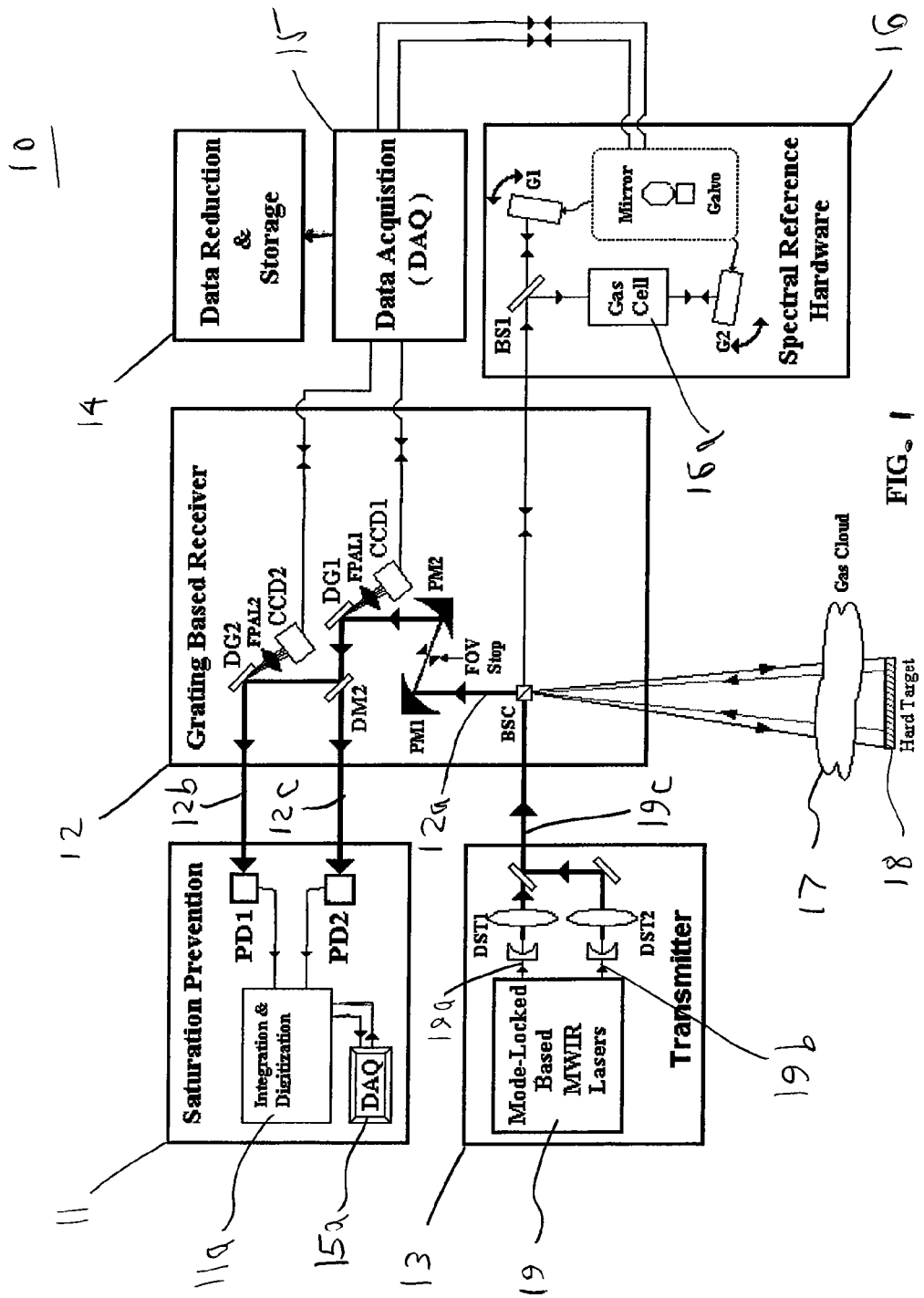
FIG. 1 is a block diagram of a remote sensing system for detecting and identifying multiple species of gas in the atmosphere, in accordance with an embodiment of the present invention.

Referring now to FIG. 1, there is shown an exemplary embodiment of the present invention. As shown, remote active sensor system 10 includes the following main components: transmitter 13, grating based receiver 12, spectral reference hardware 16, saturation prevention hardware 11, data acquisition (DAQ) module 15, and data reduction and storage module 14. Additional components, which are not shown, may also include optical scanning hardware, GPS, video cameras, optical range finders, altimeters, aircraft orientation sensors, pressure gauges, cooling units, power supplies, power meters and other diagnostic instrumentation.

Referring first to transmitter 13, two transmitter beams are generated by separate mode-locked based MWIR laser sources. As shown, the mode locked based MWIR laser sources, designated as 19 generate two beams designated, respectively, as beam 19a and beam 19b. Each beam has sufficient spectral content for 4 resolved spectral channels, one for $CH_4$ measurement and another for $CO_2$ measurement. The two beams 19a and 19b are up-collimated by divergent setting telescopes (designated as DST1 and DST2) and combined by suitable mirrors into one output beam, designated as 19c. The average power of the output beam transmitted to the atmosphere may be approximately 2-4 watts.

It will be understood that while the description of FIG. 1 is with respect to a transmitter that generates four spectral channels suitable for $CH_4$ and another four spectral channels suitable for $CO_2$, the present invention is not limited to only this configuration. Thus, other spectral channels may be generated by the present invention that are suitable for other gasses of interest in the atmosphere. In addition, it will be understood that the present invention contemplates generating multiple spectral channels for each gas of interest. Such spectral channels may include a number greater than two. There is no upper limit to the number of spectral channels that may be used by the present invention. It will be appreciated, however, that more channels generally implies more transmitted optical power.

Limiting the description to methane and carbon dioxide, as an example, methane ($CH_4$) has suitable absorption features in the 3200-3500 nanometer (nm) range. Carbon Dioxide ($CO_2$) has suitable absorption features in the 2000-2820 nm and 4300-4500 nm ranges.

The format of the spectral channels for each species of interest may include equally spaced channels of 100-150 picometer (pm) width (full width half max). One channel may be located on the center of an appropriate absorption feature, two other channels may be located on the side-lines of the same absorption feature and one further channel may be located just off the same absorption feature. Reference is made to FIG. 5 depicting an example of four channels located appropriately about the center line of a methane absorption feature at approximately 3400 nm. Considering that a suitable gas of interest may include absorption features having online and offline spacing of about 1-2 nm, considerable flexibility may be used in specifying the exact locations of these four spectral lines, in which each spectral line has a width in the order of picometers (10's to 100's).

Accordingly, transmitter 13 of remote sensor system 10, as an example, generates four spectral channels for methane and four separate spectral channels for carbon dioxide. The spectral channel wavelengths for methane are referred to herein as CH4_1, CH4_2, CH4_3 and CH4_4; the spectral channel wavelengths for carbon dioxide are referred to herein as CO2_1, CO2_2, CO2_3 and CO2_4.

Figure 2:
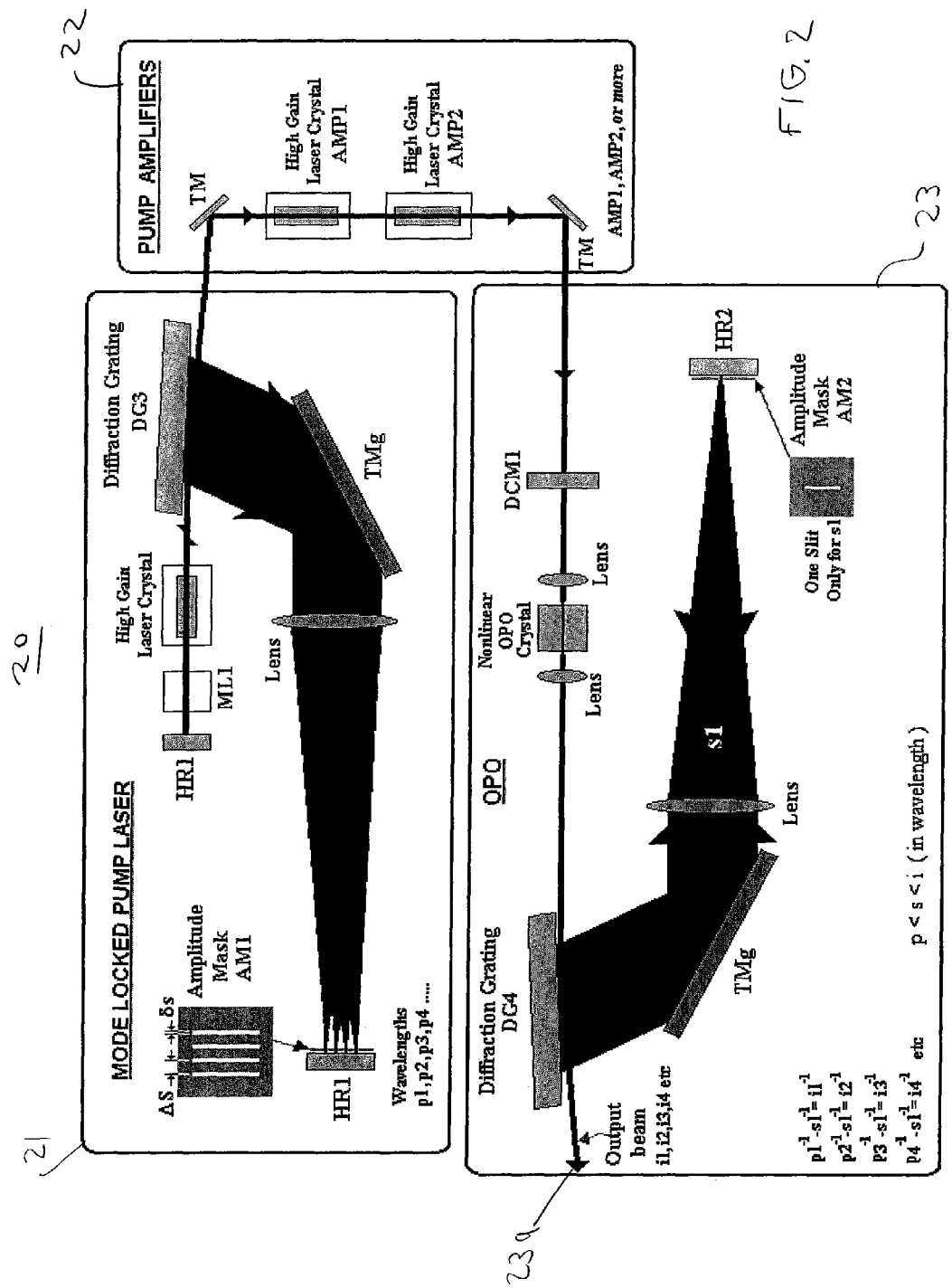
FIG. 2 is a functional block diagram depicting an optical transmitter using a mode locked pump laser for simultaneously generating multiple spectral wavelengths in a single beam of light, in accordance with an embodiment of the present invention.

Most of output beam 19c (greater than 95%) may be transmitted to the atmosphere by a beam splitting cube, designated as BSC. The remaining beam energy may be sent to the spectral reference hardware 16 for verifying that the laser output spectrum is correct. The output beam transmitted to the atmosphere passes through the column of atmosphere between the sensor platform and the ground surface, designated as 18. Between the sensor platform and the ground surface, FIG. 2 shows a gas cloud or a plume of gas, designated as 17.

The ground spot size of the output beam may be set by the divergent setting telescopes DST1 and DST2. The spot size may be set, for example, to nominally 50-150 millimeters (mm) in diameter. The spot size is determined by the aperture size of the collection optics in the grating based receiver 12. In general, the spot size is set to less than the size of the diffraction gratings (shown as DG1 and DG2).

Still referring to FIG. 1, the output beam, which impacts ground surface 18 is scattered in a Lambertian scattering pattern. A small fraction (for example, −70 dB to −110 dB) of the transmitted beam energy is backscattered by the ground surface and collected by the grating based receiver 12. The backscattered light, which is designated as 12a, is focused by an off-axis parabolic gold coated mirror (shown as PM1). The focused light is then passed through a field-of-view stop aperture (shown as FOV stop) which may limit the divergence of the collected light to approximately 150-400 micro radians (for example). This divergence limitation is important, because it provides sufficient beam separation of the four spectral sub-bands for each gas of interest. The spectral sub-bands may be measured by separate pixels of a CCD, for example. Ray tracing programs such as Code V or ZEMAX may be used to determine the appropriate divergence limitations for the FOV stop.

With respect to this exemplary embodiment of the invention, the methane channels may require 150 micro radian FOV stop for an approximate 0.5 meter CCD/grating separation, when the grating exposure has 150 mm beam diameter. After the FOV stop, the received light 12a is re-collimated by another parabolic gold coated mirror (shown as PM2). The re-collimated light is directed to a diffraction grating (shown as DG1) at a 45 degree angle of incidence, as an example. The DG1 diffracts part of the returned light associated with the $CO_2$ spectral content, while reflecting all light associated with the $CH_4$ spectral content. A second diffraction grating (shown as DG2) diffracts the light reflected off the DG1 and, thus, diffracts light associated with the $CH_4$ spectral content.

It will be appreciated that depending on the spectral content of the gasses of interest, the gas species for the diffraction gratings, DG1 and DG2, may be reversed. The shortest wavelength channels for one gas species should be diffracted by grating DG1, and the longer wavelength channels for the other gas species should be diffracted by grating DG2.

The returned light is diffracted separately by each grating DG1 and DG2 at a grating angle of approximately 76 degrees (for example) with respect to the grating normal. Each light is then focused into 4 spectral channels of each respective CCD array by way of lenses designated, respectively, as FPAL1 and FPAL2. Each CCD array (shown as CCD1 and CCD2) measures the spectral intensity of each of the 4 channels and sends data to the data acquisition (DAQ) module 15. The DAQ module controls the timing and flow of the CCD data.

It will be understood that each of the FPAL1 and FPAL2 lenses may actually be several lenses, which are needed for the CCD imaging chain. FIG. 1 shows each set of lenses as one lens. Nominally, for the resolution required in the embodiment shown in FIG. 1, the distance between the diffraction gratings (DG1 and DG2) and the CCD devices (CCD1 and CCD2) is about 0.5 meters or greater.

It will also be understood that each of the FPAL1 and FPAL2 may include a folded optical path chain comprised of several mirrors, which may be curved to provide a focusing power similar to a lens.

Portions (approximately 20-40%) of the returned light are reflected (not diffracted) off both gratings (DG1 and DG2), and continue on into the saturation prevention hardware 11. The light reflected off DG1, which is associated with $CO_2$, is passed through a dichroic mirror, designated as DM2, to form light 12c. The light associated with $CH_4$ is reflected by DM2 and passed onto grating DG2. Portions of the $CH_4$ light and $CO_2$ light reach into the saturation prevention hardware forming light 12b. Light 12b and light 12c are focused onto photodiodes PD1 and PD2, respectively, which convert light intensities into electrical signals. The electrical signals are subsequently integrated and digitized, at a rate greater than 4 MHz, by integration and digitization hardware 11a.

The hardware 11a provides signals to DAQ module 15a (which may be part of DAQ module 15) to pre-trigger the data transfers from each CCD and provide a clock reset for the integration by each CCD. If light impinging on the diffraction gratings (DG1 and DG2) have intensities which may saturate respective CCD1 or CCD2, hardware 11a sends a signal to the DAQ module to transfer respective CCD data before saturation occurs in either CCD1 or CCD2. Accordingly, the integration time window is reset by the DAQ module before saturation occurs. Such saturation events may happen, for example, when the sensor is flying over water, or flying over shiny metallic objects.

In the course of normal operation and during sensor calibration, the spectral reference hardware 16 may be used to periodically steer a portion of the transmitted laser beam back into grating based receiver 12. This may be done upon command from the DAQ module. Mirrors mounted on galvanometers (G1 and G2) may perform this task every 0.1-10 seconds nominally for collecting the spectral content of the transmitted laser beam and collecting reference spectra through a calibrated gas cell, designated as 16a. Since light reflected from these mirrors is orders of magnitude more intense than ground returned light, the saturation prevention hardware 11 may be used to trigger the DAQ module and command each of the CCDs to perform a data transfer and reset every 0.1-0.5 microseconds (for example), instead of a more typical 100-1000 microsecond integration time window during normal operations.

The DAQ module 15 may handle all the data, timing transfers and monitoring functions of the sensor and receive all the CCD signals from CCD1 and CCD2. The DAQ module may also monitor the GPS location of the aircraft, geospatial pointing data, video feeds, laser power and spectra, platform altitude and air pressure. In addition, the DAQ module may send data to the data reduction and storage system 14.

While the data reduction and storage system 14 may handle most of the data processing, the DAQ module may include a variable integration time (VIT) logic program which allows the sensor to automatically switch data collection modes when source plumes of $CH_4$ and/or $CO_2$ (for example) are encountered. This allows the sensor to perform accurate background measurements, until the sensor encounters data suggesting a gas plume of interest is present in the field-of-view of the sensor. It is desirable that system 10 is able to switch back and forth between these different data collection modes, and be able to do so independently for each gas and seamlessly, without intervention from an operator.

A more detailed description will now be provided on the mode-locked based MWIR lasers and the CCDs by referring to FIGS. 2 and 3, respectively.

As shown in FIG. 2, a mode-locked laser based transmitter, designated as 20, includes mode locked pump laser 21, pump amplifiers 22 and optical parametric oscillator (OPO) 23. The mode locked pump laser 21 may include any high gain laser crystal material, such as an Nd:YVO4, Nd:YAG, and Nd:GdVO4. The mode locked pump laser includes two high reflector (HR1) mirrors; a mode locking element (ML1); a diffraction grating (DG3); a turning mirror (TM), such as a flat gold coated mirror (TMg); a lens; and an amplitude phase mask (AM1). This laser configuration may be described as an intra-cavity spectrometer, in which the amplitude phase mask (AM1) has slits similar to slits used in grating based spectrometers.

It will be understood that transmitter 20 is described below with respect to methane only. A separate, but similar transmitter 20, with different spectral channels, may be configured for carbon dioxide.

The amplitude phase mask (AM1), shown in FIG. 2, may be a metal strip that is nominally less than 100 microns thick having precision slits, which are spaced apart to force the pump laser to obtain vacuum wavelengths of 1064.399 nm, 1064.431 nm, 1064.463 nm and 1064.495 nm inside the laser cavity. These wavelengths (at approximately 1 micron) are chosen to provide an approximate 0.28 $cm^{-1}$ spectral separation, which is centered about the peak of an Nd:YVO4 high gain material (for example). The amplitude phase mask (AM1) is located just in front of the HR1 mirror with a separation distance of nominally less than 50 microns. The widths (delta s) of the individual slits of the amplitude phase mask are configured to have line widths of 0.09-0.13 $cm^{-1}$ for each of the four enumerated central wavelengths. The distance of delta S is defined as the separation distance required to obtain the spectral separation between adjacent spectral channels, for example the separation distance between CH_1 and CH_2.

The laser crystal nominally delivers 500 milliwatts (mW) of quasi-CW output power which is mode locked by mode locking device ML1. This 500 mW of output light is sent to the pump amplifiers 22, each designated as AMP1 and AMP2, which amplify the light up to 15-20 watts. More than two amplifiers, however, may be connected in series within pump amplifier 22. The two amplifiers are sandwiched between two turning mirrors (each shown as TM).

The pumped light is then sent to the OPO cavity through a dichroic mirror (DCM1) which transmits 1064 nm light and reflects approximately 1.5 micron light. The pumped light is then focused into a nonlinear OPO crystal, such as a periodically poled lithium niobate (PPLN) crystal. The OPO crystal, which has a nominal period of 29.6-30.0 microns, is housed in a suitable oven to maintain its temperature. The PPLN crystal when pumped by the 1064 nm pump laser provides optical gain at approximately 1.5 microns, and resonates in the OPO cavity.

It will be appreciated that the PPLN period and the near IR wavelength of approximately 1.5 microns is for the methane lines, but would be different for the carbon dioxide lines, depending on which carbon dioxide lines are chosen.

Similar to the mode locked pump laser 21, the OPO cavity 23 may be based upon an intra-cavity spectrometer, with an important exception that the amplitude phase mask (AM2) and diffraction grating (DG4) cause the OPO cavity to oscillate only at 1.5 microns with a line width of 0.09-0.13 cm$^{-1}$.

As shown in FIG. 2, the OPO cavity 23 does not require a mode locking element. However, the round trip cavity time of the OPO cavity must be identical to round trip cavity time of the pump laser 21. Suitable control techniques, such as placing mirrors on PZTs may be used to effect a round trip cavity time match between the pump laser and the OPO cavity.

In the process of oscillation at approximately 1.5 microns, the OPO also generates four simultaneous MWIR wavelengths needed for the sensor output (i.e. CH4_1, CH4_2, CH4_3 and CH4_4). These MWIR wavelengths only travel in the same direction as the pump light and only bounce off the diffraction grating DG4 and become part of the OPO output beam, designated as 23a.

It will be appreciated that the OPO is about 10% efficient in the MWIR region and provides an MWIR output of 1.5-2.0 watts. All wavelengths are present in the output beam 23a and must be separated with suitable optics (not shown) to provide only the desired MWIR output spectral lines to the rest of the sensor system.

Referring next to FIGS. 3a and 3b, there is shown an exemplary pixel array device that may be used for CCD1 and CCD2 of grating based receiver 12. As an example, the CCD device, which is designated as 30, includes an array of pixels made of mercury cadmium telluride (MCT), designated as 31, and shown from the side in FIG. 3a and from the front in FIG. 3b. A one-dimensional array may also be used. A one- or 2-dimensional pixel array of approximately 1-12× approximately 32-128 pixels is required when the pixel size is 15-30 microns. A common MCT CCD 31 typically includes a much larger array, such as a 256×256 planar array.

In order to achieve data readout at rates of 1-10 kHz, an exemplary MCT CCD 31 may include a sub-windowing function, as shown in FIG. 3b, to allow programmable down selection of a predetermined number of pixels for data readout. The down selection insures that data transfer rates up to 10 kHz may be achieved by using a sub-window array of pixels. As shown, four spectral channels are included in the sub-window for the CCD used to image methane and another four spectral channels are included for the sub-window used to image carbon dioxide.

A germanium lens 32 with a focal length of 4-10 mm is included for imaging incoming light onto the MCT CCD pixels. A cold finger housing may also be included to house the MCT CCD in order to keep the CCD cold and protect its planar surface from fogging during operation. The length of the cold finger housing may be more than 15 mm long. This may cause one of the germanium lenses (referring to FPAL1 and FPAL2 in the grating based receiver 12) to be moved inside the cold finger housing. Germanium may preferably be used as the material for lens 32, because it has a high index of refraction which minimizes lens aberrations.

Figure 4A:
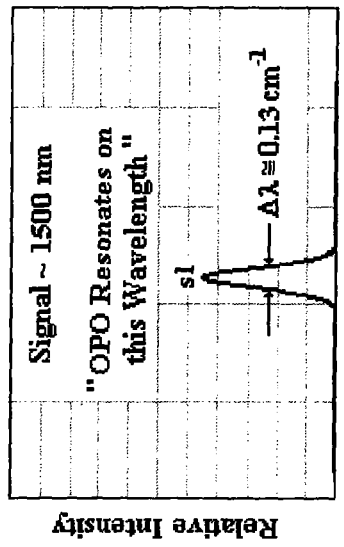
FIG. 4a shows a plot of the relative intensities of four spectral wavelengths generated by a high gain laser crystal in a mode locked laser based transmitter, in accordance with an embodiment of the present invention.
Figure 4D:
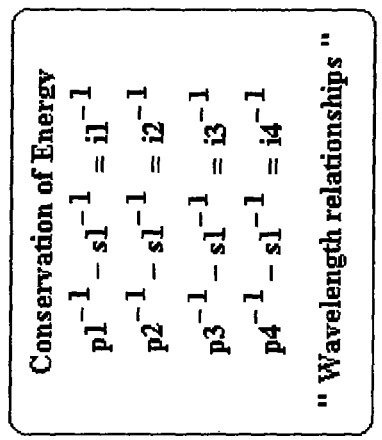
FIG. 4d shows the conservation of energy properties of the four spectral wavelengths outputted by the mode lock based laser transmitter, in accordance with an embodiment of the present invention.
Figure 4B:
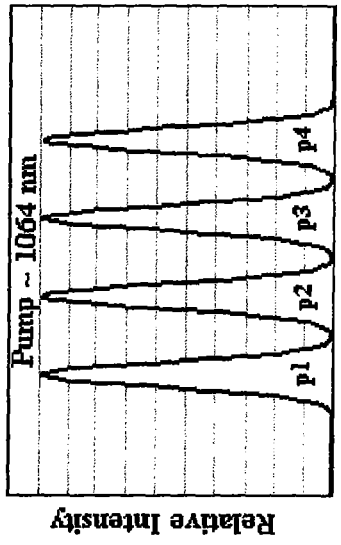
FIG. 4b shows a plot of the relative intensity of a spectral wavelength generated by an optical parametric oscillator (OPO) cavity in a mode locked laser based transmitter, in accordance with an embodiment of the present invention.
Figure 4C:
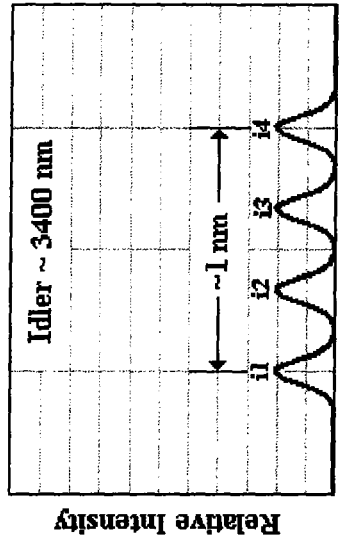
FIG. 4c shows a plot of the relative intensities of four spectral wavelengths generated by the combination of four spectral wavelengths produced by the high gain laser crystal shown in FIG. 4a and the single spectral wavelength produced by the OPO cavity shown in FIG. 4b, in accordance with an embodiment of the present invention.

Referring next to FIGS. 4a through 4d, there is shown how the spectral content of four channels is generated and derived from one mode-locked laser beam. Only one beam is transmitted by mode-locked laser beam transmitter 20 (FIG. 2) as output beam 23a. However, the output beam 23a includes four spectral channels, i1, i2, i3 and i4, which are approximately 1 nm in total width, and are adjacent, as an example, about 3400 nm (for the example of methane). In order to achieve the output beam 23a with the desired four spectral channels, the pump laser 21 (FIG. 2) generates four spectral channels, p1, p2, p3 and p4, which are approximately centered about 1064 nm (for the example of methane) and the OPO cavity 23 resonates on a wavelength designated as s1, which is approximately 1500 nm (for the example of methane). The combined oscillation between the pump laser 21 and the OPO 23 produces the idler output beam of i1, i2, i3 and i4. The conservation of energy property between the spectral content generated by the pump laser and the spectral content generated by the OPO cavity to produce the final output beam is shown in FIG. 4d.

The exemplary embodiment of the present invention in providing a CH4/CO2 sensor, may be used for the following purposes:

1) Natural gas exploration, including location of ground seeps leading to gas well location and geologic formations containing natural gas.

2) $CH_4$ and $CO_2$ quantification of industrial, commercial and agriculture emission sources such as power plants, gas pipelines, feed lots, wastewater treatment facilities, and landfills.

3) Quantification of sinks of $CO_2$ such as lakes, oceans, forests, crops and other designated $CO_2$ sequestration sites.

4) Enforcement of potential greenhouse gas emission regulations as well as treaty verification from the airborne measurement of greenhouse gases emitted from industrial sources.

5) Emergency management (FEMA) response to municipalities affected by natural disasters such as earthquakes, tornadoes, hurricanes, and floods, including rapid airborne location of damaged natural gas pipelines as well as possible locations of non-visible burning compounds releasing $CO_2$.

6) Environmental monitoring of natural sources of methane releases including high source areas such as the Arctic tundra and rainforests.

The present invention may also find applications for detecting other chemicals entering the atmosphere and, of course, the present invention is not limited to detecting methane and/or carbon dioxide. Other applications of the present invention may include:

1) Remote chemical identification of unknown chemicals entering the atmosphere.

2) Remote chemical warfare detection and identification.

3) Remote biological warfare agent detection and identification.

4) Remote measurements of water vapor for climate prediction.

5) Location of hidden military hardware emitting exhaust fumes.

6) Trace analysis and detection of compounds relating to IED (improvised explosive devices)

7) Agriculture crop health monitoring (i.e. ethane releases, $CO_2$ uptake, pesticide residuals, etc.).

8) Tracking of chemical pollutants from industrial emitters.

9) Industrial mapping of processes where leaks of certain chemicals are indicative of potential catastrophic and dangerous failures.

10) Locating illegal drug manufacturing (such as cocaine processing in Peru).

11) Atmospheric monitoring of volcanic sulfur or $CO_2$ emissions.

An exemplary data acquisition (DAQ) system for measuring, analyzing and quantifying the detected intensities of various species of gases, which may be used by the present invention, is disclosed in U.S. Pat. No. 6,995,846, issued to Kalayeh, et al. on Feb. 7, 2006. The methods and calculations disclosed therein, including methods for determining the concentration path length (CPL) of a gas of interest by using online and offline wavelengths, are incorporated herein by reference in their entireties.

As previously described, the present invention provides spectral content for detecting and measuring a species of gas or multiple species of gases. This spectral content is advantageously generated and derived from one mode-locked laser beam and one beam only is transmitted to or through the probed substance. Furthermore, the present invention provides for the generation of at least two or more resolvable spectral channels in the optical receiver of the sensor system.

Although the exemplary embodiment described above includes four spectral channels for each gas of interest, it will be understood that the present invention may include two or more spectral channels generated for each species of gas that is to be detected and measured. In fact, the present invention may generate eight or ten channels, for example, for each species of gas that is desired to be detected and measured. In addition, the present invention may include more than four resolvable spectral channels in the optical receiver of the sensor system. In fact, the present invention may resolve eight or ten channels, for example, for each returned beam. By using frequency conversion techniques on a mode-locked laser source, the present invention is able to generate any number of spectral channels desired to probe a substance of interest and use only one beam.

The modality of the present invention may also be modular and may apply to sensors configured to detect and measure two or more substances of interest. In such a case, beam combining techniques may be used to transmit more than one beam, where each beam contains more than two spectral channels. The simultaneous spectral content insures that the light in the beam probes exactly the same volumetric and/or background surface profiles at all times. This minimizes noise sources that are due to spatial/temporal spectral mismatch which are often manifested in conventional DIAL modalities. This is particularly useful when the transmitted light is moving rapidly through a substance or moving over varying hard target backgrounds, in which surface reflectivity is quickly changing.

The mode-locking techniques used by the present invention generate broader spectral profiles than other laser transmitter sources (especially CW lasers). This broader spectral profile minimizes an often encountered noise source called speckle which affects conventional DIAL modalities that use narrowband lasers.

Mode-locked lasers have higher spectral irradiance properties that lead to higher optical conversion efficiencies for other potential wavelengths of interest. Therefore, wavelengths which are hard to obtain under conventional DIAL efforts may be obtained using mode-locked laser techniques. The outputs from mode-locked lasers have shown to have good optical conversion efficiencies when used to pump nonlinear parametric conversion technologies. Accordingly, mode-locked lasers expand the ranges of wavelengths needed to probe certain substances of interest.

Although illustrated and described herein with reference to certain specific embodiments, the present invention is nevertheless not intended to be limited to the details shown. Rather, various modification may be made in the details within the scope and range of equivalents of the claims and without departing from the spirit of the invention.

What is claimed is:

1. A remote sensing system comprising:
a transmitter for transmitting a single beam of light toward a target, and
a receiver for receiving the single beam of light from the target,
wherein the transmitted single beam of light includes multiple distinct wavelengths that are simultaneously transmitted toward the target, and
the receiver is configured to simultaneously receive the multiple distinct wavelengths, and detect an intensity of each received wavelength;
the system further including:
a photodiode, connected in parallel with the receiver, for detecting intensity levels of the received single beam of light,
an integrator for integrating the detected intensity levels, and
a saturation prevention module for resetting the receiver upon reaching an intensity level by the integrator,
wherein the saturation prevention module is configured to prevent saturation of the intensity levels of the multiple distinct wavelengths detected by the receiver.

2. The remote sensing system of claim 1 wherein
the target includes at least one species of gas, and
the multiple distinct wavelengths are selected based on absorption characteristics or scattering characteristics of the one species of gas.

3. The remote sensing system of claim 2 wherein
at least one of the multiple distinct wavelengths is selected at a center of a wavelength distribution curve depicting the absorption characteristics of the species of gas, the center defined as an online wavelength, and
at least another of the multiple distinct wavelengths is selected at a wavelength location that is away from the wavelengths absorbed by the species of gas, the wavelength location defined as an offline wavelength.

4. The remote sensing system of claim 3 wherein
yet another of the multiple distinct wavelengths is selected at a location that is between the at least one online wavelength and the at least one offline wavelength.

5. The remote sensing system of claim 1 wherein
the transmitter includes a mode-locked based laser for generating the distinct multiple wavelengths in the single beam of light, and
the receiver includes a pixel array for detecting the distinct multiple wavelengths in the single beam of light.

6. The remote sensing system of claim 5 wherein
the receiver includes a diffraction grating for separating the distinct multiple wavelengths in the single beam of light, and
at least one lens or mirror is interposed between the diffraction grating and the pixel array for focusing the distinct multiple wavelengths onto the pixel array.

7. The remote sensing system of claim 5 including
a processor for receiving image intensity data from the pixel array and determining an identity of the target based on the detected distinct multiple wavelengths.

8. The remote sensing system of claim 1 including
a gas cell for receiving and testing a sample of the multiple distinct wavelengths in the single beam of light, and
means for adjusting the multiple distinct wavelengths, based on test results of the gas cell.

9. The remote sensing system of claim 1 wherein
the target includes (a) either carbon dioxide or methane, each dependent on a differential absorption wavelength, and/or (b) an aerosol dependent on differential scattering of at least one wavelength.

10. A remote sensing system comprising:
a transmitter for generating multiple beams of light,
a combiner for combining the multiple beams of light and directing the combined multiple beams toward a target, and
a receiver for receiving the combined multiple beams of light from the target,
wherein a first transmitted beam of light includes a first set of multiple distinct wavelengths that are simultaneously transmitted toward the target,
a second transmitted beam of light includes a second set of multiple distinct wavelengths that are simultaneously transmitted toward the target, and
the receiver is configured to simultaneously receive the multiple distinct wavelengths, and detect an intensity of each received wavelength.

11. The remote sensing system of claim 10 wherein the target includes at least two species of gas, and
the first set of multiple distinct wavelengths are selected based on absorption characteristics or scattering characteristics of a first species of gas, and
the second set of multiple distinct wavelengths are selected based on absorption characteristics or scattering characteristics of a second species of gas.

12. The remote sensing system of claim 11 wherein
the transmitter includes a first mode-locked based laser for generating the first set of distinct multiple wavelengths in the first transmitted beam of light,
the transmitter includes a second mode-locked based laser for generating the second set of distinct multiple wavelengths in the second transmitted beam of light,
the receiver includes a first pixel array for detecting the first set of distinct multiple wavelengths, and
the receiver includes a second pixel array for detecting the second set of distinct multiple wavelengths.

13. The remote sensing system of claim 12 wherein
the receiver includes a first diffraction grating for separating the first set of distinct multiple wavelengths, and
the receiver includes a second diffraction grating for separating the second set of distinct multiple wavelengths.

14. The remote sensing system of claim 10 wherein the combiner includes
first and second divergent setting telescopes for directing the first beam and second beam, respectively, toward a beam splitting cube, and
focusing the first and second beams to deliver the combined beam as a predetermined sized spot on the target.

15. A method for remotely detecting a plume of gas comprising the steps of:
(a) transmitting multiple beams of light toward the plume, and
(b) receiving the multiple beams of light from the plume,
wherein the step of transmitting includes
simultaneously transmitting multiple distinct wavelengths in a first beam and a second beam toward the plume, and
the step of receiving includes
simultaneously receiving the multiple distinct wavelengths from the first and second beams, and
simultaneously detecting an intensity of each received wavelength.

16. The method of claim 15 wherein the step of transmitting includes
selecting and generating the multiple distinct wavelengths based on absorption characteristics of the plume of gas.

17. The method of claim 16 wherein
at least one of the multiple distinct wavelengths is selected at a center of a wavelength distribution curve depicting the absorption characteristics of the plume of gas, the center defined as an online wavelength, and
at least another of the multiple distinct wavelengths is selected at a wavelength location that is away from the wavelengths absorbed by the plume of gas, the wavelength location defined as an offline wavelength.

18. The method of claim 17 wherein
yet another of the multiple distinct wavelengths is selected at a location that is between the at least one online wavelength and the at least one offline wavelength.

19. The method of claim 15 wherein
the step of transmitting includes using a mode-locked based laser for generating the distinct multiple wavelengths, and
the step of receiving includes
separating the distinct multiple wavelength by using a diffraction grating, and
imaging the separated distinct multiple wavelengths by using a pixel array.

* * * * *